United States Patent [19]

Hoegnelid et al.

[11] Patent Number: 5,350,412
[45] Date of Patent: Sep. 27, 1994

[54] DEVICE FOR REDUCING POWER CONSUMPTION IN MEDICAL EQUIPMENT WHICH IS IMPLANTABLE IN THE HUMAN BODY

[75] Inventors: Kurt Hoegnelid, Vaesterhaninge; Goran-Sven Budgifvars, Stockholm, both of Sweden

[73] Assignee: Siemens Elema AB, Sweden

[21] Appl. No.: 52,459

[22] Filed: Apr. 26, 1993

[30] Foreign Application Priority Data

May 21, 1992 [SE] Sweden .................... 9201602

[51] Int. Cl.$^5$ ............................ A61N 1/378
[52] U.S. Cl. ............................ 607/34; 607/16
[58] Field of Search .......... 607/16, 34, 12, 35, 607/65, 19

[56] References Cited

U.S. PATENT DOCUMENTS

| | | | |
|---|---|---|---|
| 4,237,897 | 12/1980 | Beaue et al. | 607/34 |
| 4,345,604 | 8/1982 | Renirie | 607/34 |
| 4,428,378 | 1/1984 | Anderson et al. | 607/19 |
| 4,590,941 | 5/1986 | Saulson et al. | 607/34 |
| 4,860,751 | 8/1989 | Callaghan | 607/16 |
| 5,024,222 | 6/1991 | Thacker | 607/22 |
| 5,063,927 | 11/1991 | Webb et al. | 607/18 |

OTHER PUBLICATIONS

Motorola Semiconductor Technical Data Sheet MC33102, "Sleep-Mode TM Two-State, Micropower Operational Amplifier"(1991).

Primary Examiner—Kyle L. Howell
Assistant Examiner—George Manuel
Attorney, Agent, or Firm—Hill, Steadman & Simpson

[57] ABSTRACT

A device for reducing power consumption in medical electrical equipment, implantable in the human body, having a sensor, which includes a sensor element and sensor electronic circuitry for sensing a parameter relevant to control of the equipment's in vivo operation, also has a comparator which compares the sensor element's output signal to a predesignated threshold value and switches the sensor electronic circuitry from a passive mode with low power consumption to an active mode with heavier power consumption or vice-versa, depending on the magnitude of the sensor element's signal in relation to the threshold value.

11 Claims, 1 Drawing Sheet

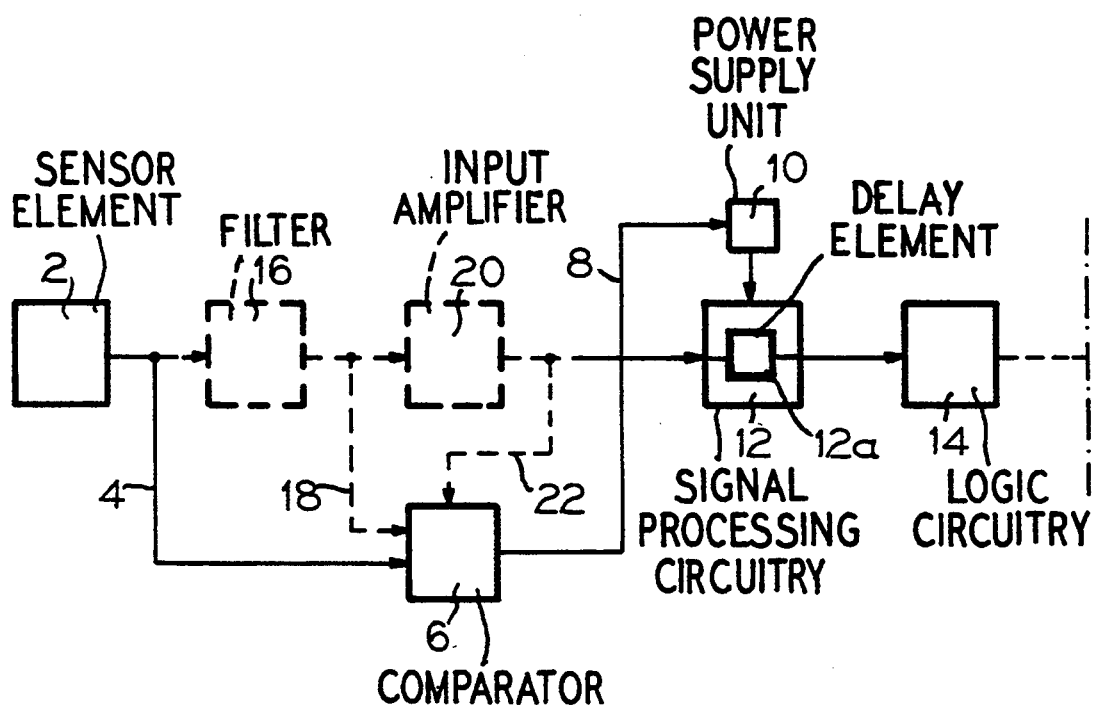

DEVICE FOR REDUCING POWER CONSUMPTION IN MEDICAL EQUIPMENT WHICH IS IMPLANTABLE IN THE HUMAN BODY

BACKGROUND OF THE INVENTION

1. Field of the Invention

The present invention relates to a device for reducing power consumption in medical electrical equipment, implantable in the human body of the type having a sensor, composed of a sensor element and sensor electronic circuitry, to sense a parameter, relevant to control of the equipment's in vivo operation, and a comparator for comparing the sensor's output signal to a predesignated threshold value.

2. Description of the Prior Art

In recent years, technicians have succeeded in making a drastic reduction in the power consumed by electrical equipment implantable in the human body. In the case of pacemakers, for example, stimulation current has been reduced from 5–10 $\mu$A to 0.5–2 $\mu$A, and the internal power consumption of pacemaker electronics has been reduced from, typically, 10 $\mu$A to, typically, 3.5 $\mu$A.

European Application 0 191 404 describes a dual sensor system for pacemaker control, having a sensor for sensing physical activity and a sensor for sensing a physiological parameter in the patient, such as partial oxygen pressure. The activity sensor is a passive element which does not require any power for operation. The electrically powered physiological sensor is only activated when the activity sensor senses physical activity by the patient above a predesignated threshold value. Thus the electrically powered physiological sensor is only in operation at times when sensing of the relevant physiological parameter is of interest, resulting in an attendant saving in energy.

An operation amplifier, which is automatically switchable between a "sleep mode", when the input signal is less than a predesignated threshold value, and an "awake mode", when the input signal exceeds the threshold value, is described in Motorola Semiconductor Technical Data Sheet MC 33102 "Sleep-Mode Two-State, Micropower Operational Amplifier," Motorola Literature Distribution, Arizona, USA, 1991. However, power consumption is still as high as about 50 $\mu$A even in the sleep mode.

SUMMARY OF THE INVENTION

It is an object of the present invention to provide a device for attaining further reduction in the internal consumption of power by the electronic circuitry in electronic equipment, implantable in the human body, such as pacemakers and pump devices.

The above object is achieved in accordance with the principles of the present invention in an implantable medical electrical apparatus including a sensor element connected to sensor electronic circuitry for sensing a parameter for use in the in vivo control of the operation of the implanted apparatus, wherein the sensor electronic circuitry is operable in a passive mode with low power consumption and in an active mode with a higher power consumption, the apparatus further including a comparator circuit having an output connected to the sensor electronic circuitry for comparing an output signal from the sensor element to a predetermined threshold. The comparator circuitry switches the sensor electronic circuitry between the passive mode and the active mode dependent on the magnitude of the output signal of the sensor element in relation to the threshold.

According to the invention, the amplifier and other sensor electronic circuitry are therefore only in the "active" mode at times in which a parameter relevant to the equipment's operation exceeds a predesignated threshold value. With a device according to the invention, power consumption is greatly lessened. Since a patient is normally completely still about 80% of the time, an activity sensor only emits an output signal about 20% of the time. The power saving attainable with the device according to the invention results in extended battery life and/or the possibility of using smaller batteries for equipment operation.

In one embodiment of the device according to the invention, the sensor is sampled at a given frequency of up to 1 kHz, i.e., the sensor senses at an interval of at least 1 msec. This means that at least 1 msec. is available for activation of the following sensor electronic circuitry, and since this circuitry is normally devised in a plurality of amplifier links, each including filters and an amplifier, at least 1 msec. is therefore available to start the first amplifier link, 2 msec. to start the second amplifier link, etc.

In a further embodiment of the device according to the invention, an input amplifier is provided between the sensor and the comparator for amplifying the sensor signal. This input amplifier, which forms the first amplifier link in sensor electronic circuitry, can also be sampled or can be in analog form.

When sampling can occur at different points in time in the course of the sensor signal, the output signal may contain signals related to the sampling procedure itself and caused by aliasing phenomena or aliasing distortion during sampling. In another embodiment of the device according to the invention, a low-pass filter is therefore provided between the sensor and the comparator to filter out rapid fluctuations in the sensor signal so they are not erroneously sampled and interpreted as slow signals.

In another embodiment of the device according to the invention, a low level current, i.e., about 10 nA, is fed to each amplifier or some other sub-element in its "resting" or "passive mode", such as an A/D converter, a comparator, etc., in the sensor electronic circuitry. In this instance, the comparator's output signal is devised to control a power supply unit for the sensor electronic circuitry performing signal processing, whereby the current is increased, typically to about 100 nA/amplifier or sub-element in the sensor electronic circuitry, when the sensor signal exceeds the threshold value.

The device according to the invention can also be devised so the comparator simply switches the sensor electronic circuitry on or off, depending on the magnitude of the sensor signal.

In another embodiment of the device according to the invention, a delay circuit is provided to delay switching from a mode with heavier power consumption to a mode with low power consumption after a given period of time has elapsed after the sensor signal drops below the threshold value, so as to keep the sensor electronic circuitry and other equipment from constantly being switched between their operating modes because of rapid fluctuations in the sensor signal.

The device according to the invention can be used to advantage in cardiac signal detectors, since the cardiac signal is normally on a constant "null" level throughout a large part of its period. In this instance, the sensor element itself consists of an element for sensing intracardial electrical signals.

In the application of the device according to the invention to an activity sensor, the sensor element can be a pressure- or movement- sensing sensor element, such as a piezoelectric sensor element, but other kinds of sensor elements for sensing other parameters in the body could also be employed.

DESCRIPTION OF THE DRAWING

The single FIGURE is a schematic block diagram of a device for reducing power consumption in medical electrical equipment, constructed in accordance with the principles of the present invention.

DESCRIPTION OF THE PREFERRED EMBODIMENTS

The device shown in the drawing includes a sensor element 2 which senses activity in a patient. In the simplest form of the device, the output signal from the sensor element 2 is fed to a comparator 6 via a line 4 for comparison with a predesignated threshold value. The comparator 6, via a line 8, controls a current measurement unit 10 for signal processing equipment in sensor electronic (signal processing) circuitry 12 which, in turn, is connected to logic circuitry 14 in the pacemaker. The rest of the pacemaker is not described herein, since it is not part of the invention.

Thus, the sensor signal is compared in the comparator 6 to a threshold value. The signal processing circuitry 12, which normally includes an A/D converter, is powered by the power supply unit 10 with a low current, typically about 10 nA per amplifier or per some other sub-element in the sensor electronic circuitry, in a "resting" mode, when the sensor signal is less that the predesignated threshold value. However, when the sensor signal exceeds the threshold value, the comparator 6 causes the power supply unit 10 to deliver a larger current, typically about 100 nA per amplifier per some other subelement in the sensor electronic circuitry, to the signal processing circuit 12 which is thereby switched to a active operating mode.

A typical magnitude for the sensor signal when activity is detected in the patient is 100 mV, and the comparator's predesignated threshold value can be 30 to 40 mV.

When the sensor signal again drops below the threshold value, the signal processing circuit is switched to its resting mode with low power consumption, this re-switching preferably occurring with a certain delay to keep the signal processing equipment from continuously switching back and forth between the operating modes when the sensor signal fluctuates rapidly. For this purpose, the signal processing circuitry contains a schematically indicated delay circuit 12a.

A filter 16 could possibly be installed to filter the sensor signal before it reaches the comparator 6 via the line 18. When the sensor signal, in certain versions of the device according to the invention, is sampled at a given frequency, not exceeding 1 kHz, this sampling can give rise to aliasing phenomena or aliasing distortion in the signal fed to the comparator because the sampling is made at different points in time in the course of the sensor signal. Rapid signal fluctuations are therefore filtered out, appropriately with the filter 16 which then consists of a low-pass filter, i.e., an anti-aliasing filter, before the signal is fed to the comparator 6 via the line 18.

An input amplifier 20, possibly with a bandpass filter, can also be provided to amplify the signal before it is fed to the comparator 6 via the line 22. The input amplifier 20 is permanently enabled in this version.

The invention was described above in conjunction with an activity sensor for a pacemaker. However, the invention can also be utilized in a cardiac signal detector, wherein the sensor is then devised to record an intracardial ECG (IECG), the sensor element serving as a sensing element for intracardial electrical signals, i.e., normally picked up by the cardiac electrode.

The device according to the invention achieves a considerable power saving.

An activity sensor for a pacemaker, comprising a piezoelectric sensor element and attendant sensor electronic circuitry, draws about 1 $\mu$A. The first amplifier stage in the sensor electronics draws about $\frac{1}{3}$ of that current, i.e., about 300 nA whereas the remaining 700 nA are utilized by the rest of the sensor electronics. With the device according to the invention, utilized with such an activity sensor, assuming that the said first amplifier stage is permanently enabled and assuming that the patient is still about 80% of the time, which are reasonable assumptions, the sensor's total power consumption amounts to about 440 nA, i.e., power consumption is more than halved.

Even a cardiac signal detector draws a current of about 1 $\mu$A. With the invention applied in an analogous manner to such a cardiac signal detector, assuming that the first amplifier stage is a permanently enabled input amplifier even in this instance and that the detector electronics are disabled half the time, which are reasonable assumptions, total power consumption becomes 650 nA, i.e., the power saving amounts to 350 nA.

The total power saving in the activity sensor and the cardiac signal detector would therefore amount to about 900 nA. It should be noted that this is a conservative estimate because the estimate assumed that a permanently enabled input amplifier would be required.

As a result of this reduction in power consumption, the life of the batteries can be extended, and/or the use of smaller batteries becomes a possibility.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for reducing power consumption in medical electrical equipment implantable in the human body, said device comprising:

sensor means, including a sensor element connected to sensor electronic circuitry, for sensing a parameter for use in the in vivo control of the operation of said medical electrical equipment, said sensor electronic circuitry being operable in a passive mode with low power consumption and an active mode with a higher power consumption;

said sensor electronic circuitry including a power supply unit; and comparator means, having an output connected to said power supply unit, for comparing an output signal from said sensor element to a predetermined threshold and for controlling said power supply unit to switch said sensor electronic circuitry between said passive mode and said active mode dependent on the magnitude of said output signal of said sensor element in relation to said threshold.

2. A device as claimed in claim 1 wherein said sensor electronic circuitry includes means for sampling said output signal of said sensor element at a predetermined sampling frequency.

3. A device as claimed in claim 2 further comprising low-pass filter means connected between said sensor element and said comparator means for removing rapid fluctuations in said output signal of said sensor element.

4. A device as claimed in claim 1 further comprising input amplifier means connected between said sensor element and said comparator for amplifying said output signal of said sensor element.

5. A device as claimed in claim 1 further comprising delay means for delaying switching of said sensor electronic circuitry from said active mode to said passive mode by a selected period of time after said output signal of said sensor element falls below said threshold.

6. A device as claimed in claim 1 wherein said signal from said comparator means enable said sensor electronic circuitry when said output signal of said sensor element exceeds said threshold and disenables said sensor electronic circuitry when said output signal of said sensor element falls below said threshold.

7. A device as claimed in claim 1 wherein said sensor means comprises a cardiac signal detector for detecting ECG signals, and wherein said sensor element comprises an element for sensing intracardial electrical signals.

8. A device as claimed in claim 1 wherein said sensor element comprises a pressure-sensing activity sensor element.

9. A device as claimed in claim 8 wherein said sensor element is a piezoelectric element.

10. A device as claimed in claim 1 wherein said sensor element comprises a movement-sensing activity sensor element.

11. A device as claimed in claim 10 wherein said sensor element is a piezoelectric element.

* * * * *